United States Patent
Royo García et al.

(10) Patent No.: US 9,914,980 B2
(45) Date of Patent: Mar. 13, 2018

(54) PRIMERS FOR THE DETECTION AND TYPING OF CARBAPENEMASE-PRODUCING BACTERIAL STRAINS, AND DETECTION METHOD AND KIT

(71) Applicant: Fundación Para El Fomento De La Investigación Sanitaria Y Biomédica De La Communitat Valenciana, Valencia (ES)

(72) Inventors: Gloria Royo García, Valencia (ES); Juan Carlos Rodríguez Díaz, Valencia (ES); Antonio José Galiana Cabrera, Valencia (ES)

(73) Assignee: Fundación Para El Fomento De La Investigación Sanitaria Y Biomédica De La Communitat Valenciana, Valencia (ES)

( * ) Notice: Subject to any disclaimer, the term of this patent is extended or adjusted under 35 U.S.C. 154(b) by 0 days.

(21) Appl. No.: 14/758,458

(22) PCT Filed: Feb. 28, 2014

(86) PCT No.: PCT/IB2014/000230
§ 371 (c)(1),
(2) Date: Jun. 29, 2015

(87) PCT Pub. No.: WO2014/102761
PCT Pub. Date: Jul. 3, 2014

(65) Prior Publication Data
US 2016/0122805 A1 May 5, 2016

(30) Foreign Application Priority Data

Dec. 31, 2012 (ES) .................. 201232077

(51) Int. Cl.
*C12Q 1/68* (2018.01)
(52) U.S. Cl.
CPC ....... *C12Q 1/689* (2013.01); *C12Q 2600/156* (2013.01); *C12Q 2600/16* (2013.01)
(58) Field of Classification Search
CPC ............. C12C 2600/156; C12C 1/689; C12C 2600/16
USPC ....................................................... 435/91.2
See application file for complete search history.

(56) References Cited

U.S. PATENT DOCUMENTS

| 2007/0042982 A1* | 2/2007 | Bentwich ............... C12Q 1/689 514/44 A |
| 2009/0163382 A1 | 6/2009 | Oh et al. |
| 2009/0317807 A1 | 12/2009 | Hanson |
| 2012/0129180 A1 | 5/2012 | Kirveskari et al. |
| 2013/0065790 A1 | 3/2013 | Vos |

FOREIGN PATENT DOCUMENTS

| CN | 1396271 A | 2/2003 |
| WO | 2007140004 A2 | 12/2007 |
| WO | 2010130882 A1 | 11/2010 |
| WO | 2011138402 A1 | 11/2011 |

OTHER PUBLICATIONS

Swayne, Rosemary, et al.; "Utility of a novel multiplex TaqMan PCR assay for metallo-beta-lactamase genes plus other TaqMan assays in detecting genes encoding serine carbapenemases and clinically significant extended-spectrum beta-lactamases," International Journal of Antimicrobial Agents, 2013, pp. 352-356, vol. 42.
Iwaya, Akira, et al.; "Rapid and quantitative detection of blood Serratia marcescens by a real-time PCR assay: Its clinical application and evaluation in a mouse infection model," FEMS Microbiology Letters, 2005, pp. 163-170, vol. 248.
Monteiro, Jussimara, et al.; "Rapid detection of carbapenemase genes by multiplex real-time PCR," Journal of Antimicrobial Chemotherapy, 2012, pp. 906-909, vol. 67.
Doyle, Diana, et al.; "Laboratory Detection of Enterobacteriaceae That Produce Carbapenemases," Journal of Clinical Microbiology, 2012, pp. 3877-3880, vol. 50.
Ellington, Matthew J., et al.; "Multiplex PCR for rapid detection of genes encoding acquired metallo-beta-actamases," Journal of Antimicrobial Chemotherapy, 2007, pp. 321-322, vol. 59.
Swayne, R.L., et al.; "Real-time TaqMan PCR for rapid detection of genes encoding five types of non-metallo-(class A and D)carbapenemases in Enterobacteriaceae," International Journal of Antimicrobial Agents, 2011, pp. 35-38, vol. 29.
International Search Report/Written Opinion, dated Nov. 28, 2014.

* cited by examiner

*Primary Examiner* — Cynthia B Wilder
(74) *Attorney, Agent, or Firm* — Tristan A. Fuierer; Moore & Van Allen, PLLC

(57) ABSTRACT

Some pairs of primers are provided, being used for detection of carbapenemase genes and carbapenemase-producing bacterial strains, and a diagnosis method using said set of primers. Furthermore, there is also disclosed, preferably, the use of probes within each amplification reaction, more preferably multiplex PCR, for selective identification and detection of carbapenemase genes from a biological sample. The primers object of this invention may be used for preparing a kit for carbapenemase genes identification and detection, preferably carbapenemases contained in bacterial strains producing said enzymes.

24 Claims, 4 Drawing Sheets

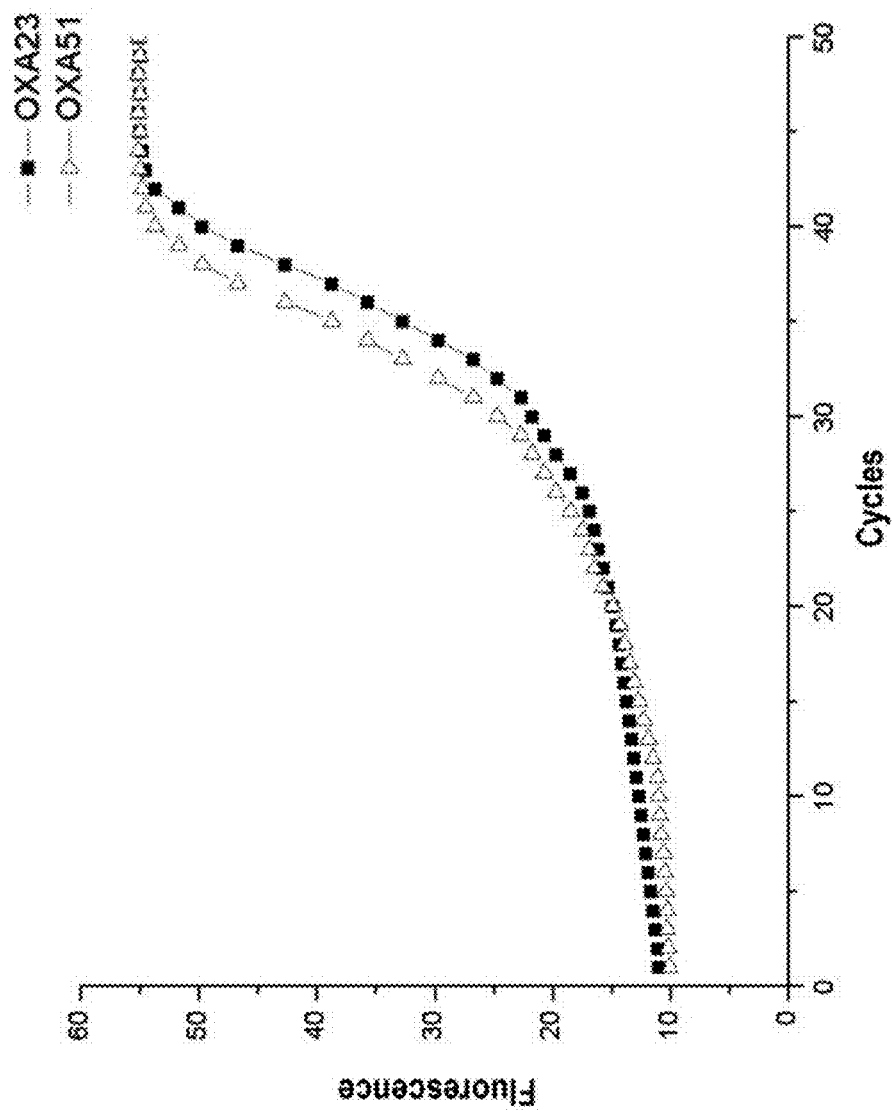

```
                        SEQUENCE LISTING

<160> NUMBER OF SEQ ID NOS: 77

<210> SEQ ID NO 1
<211> LENGTH: 18
<212> TYPE: DNA
<213> ORGANISM: Artificial Sequence
<220> FEATURE:
<223> OTHER INFORMATION: Synthetic Construct

<400> SEQUENCE: 1
tcggtaatgc tgaaattg                                                       18

<210> SEQ ID NO 2
<211> LENGTH: 19
<212> TYPE: DNA
<213> ORGANISM: Artificial Sequence
<220> FEATURE:
<223> OTHER INFORMATION: Synthetic Construct

<400> SEQUENCE: 2
ctgtgtatgt gctaattgg                                                      19

<210> SEQ ID NO 3
<211> LENGTH: 27
<212> TYPE: DNA
<213> ORGANISM: Artificial Sequence
<220> FEATURE:
<223> OTHER INFORMATION: Synthetic Construct

<400> SEQUENCE: 3
aactctacct cttgaatagg cgtaacc                                             27

<210> SEQ ID NO 4
<211> LENGTH: 19
<212> TYPE: DNA
<213> ORGANISM: Artificial Sequence
<220> FEATURE:
<223> OTHER INFORMATION: Synthetic Construct

<400> SEQUENCE: 4
ccttcaaaat gcttaatgc                                                      19

<210> SEQ ID NO 5
<211> LENGTH: 18
<212> TYPE: DNA
<213> ORGANISM: Artificial Sequence
<220> FEATURE:
<223> OTHER INFORMATION: Synthetic Construct

<400> SEQUENCE: 5
tagggtcatg tccttttc                                                       18

<210> SEQ ID NO 6
<211> LENGTH: 22
<212> TYPE: DNA
<213> ORGANISM: Artificial Sequence
<220> FEATURE:
<223> OTHER INFORMATION: Synthetic Construct

<400> SEQUENCE: 6
```

```
caccataagg caaccaccac ag                                            22

<210> SEQ ID NO 7
<211> LENGTH: 18
<212> TYPE: DNA
<213> ORGANISM: Artificial Sequence
<220> FEATURE:
<223> OTHER INFORMATION: Synthetic Construct

<400> SEQUENCE: 7
tgagcatagt atgagtcg                                                 18

<210> SEQ ID NO 8
<211> LENGTH: 18
<212> TYPE: DNA
<213> ORGANISM: Artificial Sequence
<220> FEATURE:
<223> OTHER INFORMATION: Synthetic Construct

<400> SEQUENCE: 8
tgaccatcat atgtgaca                                                 18

<210> SEQ ID NO 9
<211> LENGTH: 27
<212> TYPE: DNA
<213> ORGANISM: Artificial Sequence
<220> FEATURE:
<223> OTHER INFORMATION: Synthetic Construct

<400> SEQUENCE: 9
ttccacaagt gaataactca atcatcg                                       27

<210> SEQ ID NO 10
<211> LENGTH: 18
<212> TYPE: DNA
<213> ORGANISM: Artificial Sequence
<220> FEATURE:
<223> OTHER INFORMATION: Synthetic Construct

<400> SEQUENCE: 10
tgcaggctta tgtcgatg                                                 18

<210> SEQ ID NO 11
<211> LENGTH: 19
<212> TYPE: DNA
<213> ORGANISM: Artificial Sequence
<220> FEATURE:
<223> OTHER INFORMATION: Synthetic Construct

<400> SEQUENCE: 11
cttcgaaagc ggaaatctc                                                19

<210> SEQ ID NO 12
<211> LENGTH: 21
<212> TYPE: DNA
<213> ORGANISM: Artificial Sequence
<220> FEATURE:
<223> OTHER INFORMATION: Synthetic Construct

<400> SEQUENCE: 12
cgcagccaga actggtcgat c                                             21

<210> SEQ ID NO 13
<211> LENGTH: 18
<212> TYPE: DNA
```

```
<213> ORGANISM: Artificial Sequence
<220> FEATURE:
<223> OTHER INFORMATION: Synthetic Construct

<400> SEQUENCE: 13
cctgatcggc ttatccac                                                  18

<210> SEQ ID NO 14
<211> LENGTH: 18
<212> TYPE: DNA
<213> ORGANISM: Artificial Sequence
<220> FEATURE:
<223> OTHER INFORMATION: Synthetic Construct

<400> SEQUENCE: 14
gtacgttcga tgccttga                                                  18

<210> SEQ ID NO 15
<211> LENGTH: 21
<212> TYPE: DNA
<213> ORGANISM: Artificial Sequence
<220> FEATURE:
<223> OTHER INFORMATION: Synthetic Construct

<400> SEQUENCE: 15
tagatccgcc gacgaggttc t                                              21

<210> SEQ ID NO 16
<211> LENGTH: 24
<212> TYPE: DNA
<213> ORGANISM: Artificial Sequence
<220> FEATURE:
<223> OTHER INFORMATION: Synthetic Construct

<400> SEQUENCE: 16
aagcgagtac tgactatary attc                                           24

<210> SEQ ID NO 17
<211> LENGTH: 19
<212> TYPE: DNA
<213> ORGANISM: Artificial Sequence
<220> FEATURE:
<223> OTHER INFORMATION: Synthetic Construct

<400> SEQUENCE: 17
caggttaacg gcgaaatag                                                 19

<210> SEQ ID NO 18
<211> LENGTH: 21
<212> TYPE: DNA
<213> ORGANISM: Artificial Sequence
<220> FEATURE:
<223> OTHER INFORMATION: Synthetic Construct

<400> SEQUENCE: 18
cgtccaactc caaccaaccg a                                              21

<210> SEQ ID NO 19
<211> LENGTH: 18
<212> TYPE: DNA
<213> ORGANISM: Artificial Sequence
<220> FEATURE:
<223> OTHER INFORMATION: Synthetic Construct

<400> SEQUENCE: 19
cgatcattcc ctgggatg                                                  18
```

<210> SEQ ID NO 20
<211> LENGTH: 18
<212> TYPE: DNA
<213> ORGANISM: Artificial Sequence
<220> FEATURE:
<223> OTHER INFORMATION: Synthetic Construct

<400> SEQUENCE: 20
gagacgacct gatagcag                                                    18

<210> SEQ ID NO 21
<211> LENGTH: 20
<212> TYPE: DNA
<213> ORGANISM: Artificial Sequence
<220> FEATURE:
<223> OTHER INFORMATION: Synthetic Construct

<400> SEQUENCE: 21
ccgcgacgca tcaagaactg                                                  20

<210> SEQ ID NO 22
<211> LENGTH: 20
<212> TYPE: DNA
<213> ORGANISM: Artificial Sequence
<220> FEATURE:
<223> OTHER INFORMATION: Synthetic Construct

<400> SEQUENCE: 22
gctgtatcat aacaagttgc                                                  20

<210> SEQ ID NO 23
<211> LENGTH: 18
<212> TYPE: DNA
<213> ORGANISM: Artificial Sequence
<220> FEATURE:
<223> OTHER INFORMATION: Synthetic Construct

<400> SEQUENCE: 23
cgatctgagg ctcaattc                                                    18

<210> SEQ ID NO 24
<211> LENGTH: 23
<212> TYPE: DNA
<213> ORGANISM: Artificial Sequence
<220> FEATURE:
<223> OTHER INFORMATION: Synthetic Construct

<400> SEQUENCE: 24
cagtcagcgt atcgtcaagc aag                                              23

<210> SEQ ID NO 25
<211> LENGTH: 22
<212> TYPE: DNA
<213> ORGANISM: Artificial Sequence
<220> FEATURE:
<223> OTHER INFORMATION: Synthetic Construct

<400> SEQUENCE: 25
gtgggagaaa gatatgactt ta                                               22

<210> SEQ ID NO 26
<211> LENGTH: 18
<212> TYPE: DNA
<213> ORGANISM: Artificial Sequence
<220> FEATURE:

```
<223> OTHER INFORMATION: Synthetic Construct

<400> SEQUENCE: 26
tcgacctgtg ttccaata                                                   18

<210> SEQ ID NO 27
<211> LENGTH: 27
<212> TYPE: DNA
<213> ORGANISM: Artificial Sequence
<220> FEATURE:
<223> OTHER INFORMATION: Synthetic Construct

<400> SEQUENCE: 27
tgtcagcagt tccagtatat caagagc                                         27

<210> SEQ ID NO 28
<211> LENGTH: 19
<212> TYPE: DNA
<213> ORGANISM: Artificial Sequence
<220> FEATURE:
<223> OTHER INFORMATION: Synthetic Construct

<400> SEQUENCE: 28
gttggaatgc tcactttac                                                  19

<210> SEQ ID NO 29
<211> LENGTH: 18
<212> TYPE: DNA
<213> ORGANISM: Artificial Sequence
<220> FEATURE:
<223> OTHER INFORMATION: Synthetic Construct

<400> SEQUENCE: 29
ttcgcccgtt taagatta                                                   18

<210> SEQ ID NO 30
<211> LENGTH: 26
<212> TYPE: DNA
<213> ORGANISM: Artificial Sequence
<220> FEATURE:
<223> OTHER INFORMATION: Synthetic Construct

<400> SEQUENCE: 30
aatccttgct gcttattctc attcca                                          26

<210> SEQ ID NO 31
<211> LENGTH: 20
<212> TYPE: DNA
<213> ORGANISM: Artificial Sequence
<220> FEATURE:
<223> OTHER INFORMATION: Synthetic Construct

<400> SEQUENCE: 31
gaacgtattg atttcggtaa                                                 20

<210> SEQ ID NO 32
<211> LENGTH: 18
<212> TYPE: DNA
<213> ORGANISM: Artificial Sequence
<220> FEATURE:
<223> OTHER INFORMATION: Synthetic Construct

<400> SEQUENCE: 32
ctgtgtatgt gccaattg                                                   18
```

```
<210> SEQ ID NO 33
<211> LENGTH: 26
<212> TYPE: DNA
<213> ORGANISM: Artificial Sequence
<220> FEATURE:
<223> OTHER INFORMATION: Synthetic Construct

<400> SEQUENCE: 33
aactctacct cttgaatagg cgtgac                                          26

<210> SEQ ID NO 34
<211> LENGTH: 19
<212> TYPE: DNA
<213> ORGANISM: Artificial Sequence
<220> FEATURE:
<223> OTHER INFORMATION: Synthetic Construct

<400> SEQUENCE: 34
ccacaagtag gttggttaa                                                  19

<210> SEQ ID NO 35
<211> LENGTH: 22
<212> TYPE: DNA
<213> ORGANISM: Artificial Sequence
<220> FEATURE:
<223> OTHER INFORMATION: Synthetic Construct

<400> SEQUENCE: 35
ccctaaattt tctaacgact ta                                              22

<210> SEQ ID NO 36
<211> LENGTH: 25
<212> TYPE: DNA
<213> ORGANISM: Artificial Sequence
<220> FEATURE:
<223> OTHER INFORMATION: Synthetic Construct

<400> SEQUENCE: 36
agaaccagac attccttgct tcatt                                           25

<210> SEQ ID NO 37
<211> LENGTH: 18
<212> TYPE: DNA
<213> ORGANISM: Artificial Sequence
<220> FEATURE:
<223> OTHER INFORMATION: Synthetic Construct

<400> SEQUENCE: 37
taggcgaygc tatgaaag                                                   18

<210> SEQ ID NO 38
<211> LENGTH: 18
<212> TYPE: DNA
<213> ORGANISM: Artificial Sequence
<220> FEATURE:
<223> OTHER INFORMATION: Synthetic Construct

<400> SEQUENCE: 38
cttgggtacc gatatctg                                                   18

<210> SEQ ID NO 39
<211> LENGTH: 26
<212> TYPE: DNA
<213> ORGANISM: Artificial Sequence
<220> FEATURE:
<223> OTHER INFORMATION: Synthetic Construct
```

<400> SEQUENCE: 39
aaccaacacg cttcacttca ttagac                26

<210> SEQ ID NO 40
<211> LENGTH: 19
<212> TYPE: DNA
<213> ORGANISM: Artificial Sequence
<220> FEATURE:
<223> OTHER INFORMATION: Synthetic Construct

<400> SEQUENCE: 40
catcgacgtt caagattcc                        19

<210> SEQ ID NO 41
<211> LENGTH: 18
<212> TYPE: DNA
<213> ORGANISM: Artificial Sequence
<220> FEATURE:
<223> OTHER INFORMATION: Synthetic Construct

<400> SEQUENCE: 41
ctcccactgc ttgtaagg                         18

<210> SEQ ID NO 42
<211> LENGTH: 20
<212> TYPE: DNA
<213> ORGANISM: Artificial Sequence
<220> FEATURE:
<223> OTHER INFORMATION: Synthetic Construct

<400> SEQUENCE: 42
aacagcctga tcgccttcga                       20

<210> SEQ ID NO 43
<211> LENGTH: 18
<212> TYPE: DNA
<213> ORGANISM: Artificial Sequence
<220> FEATURE:
<223> OTHER INFORMATION: Synthetic Construct

<400> SEQUENCE: 43
gtgccgatat accaggag                         18

<210> SEQ ID NO 44
<211> LENGTH: 19
<212> TYPE: DNA
<213> ORGANISM: Artificial Sequence
<220> FEATURE:
<223> OTHER INFORMATION: Synthetic Construct

<400> SEQUENCE: 44
cttcgaatgc ggaaatctc                        19

<210> SEQ ID NO 45
<211> LENGTH: 21
<212> TYPE: DNA
<213> ORGANISM: Artificial Sequence
<220> FEATURE:
<223> OTHER INFORMATION: Synthetic Construct

<400> SEQUENCE: 45
ccacgcagcc agaattgatc g                     21

<210> SEQ ID NO 46
<211> LENGTH: 18

```
<212> TYPE: DNA
<213> ORGANISM: Artificial Sequence
<220> FEATURE:
<223> OTHER INFORMATION: Synthetic Construct

<400> SEQUENCE: 46
tccgrcttta ccagattg                                                 18

<210> SEQ ID NO 47
<211> LENGTH: 18
<212> TYPE: DNA
<213> ORGANISM: Artificial Sequence
<220> FEATURE:
<223> OTHER INFORMATION: Synthetic Construct

<400> SEQUENCE: 47
cacgctgtat caatcaaa                                                 18

<210> SEQ ID NO 48
<211> LENGTH: 23
<212> TYPE: DNA
<213> ORGANISM: Artificial Sequence
<220> FEATURE:
<223> OTHER INFORMATION: Synthetic Construct

<400> SEQUENCE: 48
caactcatca ccatcacgga caa                                           23

<210> SEQ ID NO 49
<211> LENGTH: 21
<212> TYPE: DNA
<213> ORGANISM: Artificial Sequence
<220> FEATURE:
<223> OTHER INFORMATION: Synthetic Construct

<400> SEQUENCE: 49
tggagtatat cttcatacct c                                             21

<210> SEQ ID NO 50
<211> LENGTH: 18
<212> TYPE: DNA
<213> ORGANISM: Artificial Sequence
<220> FEATURE:
<223> OTHER INFORMATION: Synthetic Construct

<400> SEQUENCE: 50
cttcgtgtct tcttcaga                                                 18

<210> SEQ ID NO 51
<211> LENGTH: 27
<212> TYPE: DNA
<213> ORGANISM: Artificial Sequence
<220> FEATURE:
<223> OTHER INFORMATION: Synthetic Construct

<400> SEQUENCE: 51
aggcttgatt attatccaga actacca                                       27

<210> SEQ ID NO 52
<211> LENGTH: 19
<212> TYPE: DNA
<213> ORGANISM: Artificial Sequence
<220> FEATURE:
<223> OTHER INFORMATION: Synthetic Construct

<400> SEQUENCE: 52
```

```
cttcgaatgt cttagtagc                                                    19
```

<210> SEQ ID NO 53
<211> LENGTH: 18
<212> TYPE: DNA
<213> ORGANISM: Artificial Sequence
<220> FEATURE:
<223> OTHER INFORMATION: Synthetic Construct

<400> SEQUENCE: 53

```
tcggcttcat agtcttag                                                     18
```

<210> SEQ ID NO 54
<211> LENGTH: 22
<212> TYPE: DNA
<213> ORGANISM: Artificial Sequence
<220> FEATURE:
<223> OTHER INFORMATION: Synthetic Construct

<400> SEQUENCE: 54

```
accgttgtca ttgtctcttc gc                                                22
```

<210> SEQ ID NO 55
<211> LENGTH: 18
<212> TYPE: DNA
<213> ORGANISM: Artificial Sequence
<220> FEATURE:
<223> OTHER INFORMATION: Synthetic Construct

<400> SEQUENCE: 55

```
ttggctaaag ggaaacac                                                     18
```

<210> SEQ ID NO 56
<211> LENGTH: 18
<212> TYPE: DNA
<213> ORGANISM: Artificial Sequence
<220> FEATURE:
<223> OTHER INFORMATION: Synthetic Construct

<400> SEQUENCE: 56

```
cgacggcata gtcatttg                                                     18
```

<210> SEQ ID NO 57
<211> LENGTH: 20
<212> TYPE: DNA
<213> ORGANISM: Artificial Sequence
<220> FEATURE:
<223> OTHER INFORMATION: Synthetic Construct

<400> SEQUENCE: 57

```
catacvctcc gcaggttccg                                                   20
```

<210> SEQ ID NO 58
<211> LENGTH: 19
<212> TYPE: DNA
<213> ORGANISM: Artificial Sequence
<220> FEATURE:
<223> OTHER INFORMATION: Synthetic Construct

<400> SEQUENCE: 58

```
gggaatgttc tcaatgcta                                                    19
```

<210> SEQ ID NO 59
<211> LENGTH: 18
<212> TYPE: DNA
<213> ORGANISM: Artificial Sequence
<220> FEATURE:
<223> OTHER INFORMATION: Synthetic Construct

<400> SEQUENCE: 59
cacctacaac ccaatcag                                                    18

<210> SEQ ID NO 60
<211> LENGTH: 25
<212> TYPE: DNA
<213> ORGANISM: Artificial Sequence
<220> FEATURE:
<223> OTHER INFORMATION: Synthetic Construct

<400> SEQUENCE: 60
cgagcatcac cagttgtatt acctt                                            25

<210> SEQ ID NO 61
<211> LENGTH: 23
<212> TYPE: DNA
<213> ORGANISM: Artificial Sequence
<220> FEATURE:
<223> OTHER INFORMATION: Synthetic Construct

<400> SEQUENCE: 61
acccatcaca actaaatata aag                                              23

<210> SEQ ID NO 62
<211> LENGTH: 24
<212> TYPE: DNA
<213> ORGANISM: Artificial Sequence
<220> FEATURE:
<223> OTHER INFORMATION: Synthetic Construct

<400> SEQUENCE: 62
cgttcaagra taatattagt agca                                             24

<210> SEQ ID NO 63
<211> LENGTH: 20
<212> TYPE: DNA
<213> ORGANISM: Artificial Sequence
<220> FEATURE:
<223> OTHER INFORMATION: Synthetic Construct

<400> SEQUENCE: 63
agcdgcagca gccatatcac                                                  20

<210> SEQ ID NO 64
<211> LENGTH: 18
<212> TYPE: DNA
<213> ORGANISM: Artificial Sequence
<220> FEATURE:
<223> OTHER INFORMATION: Synthetic Construct

<400> SEQUENCE: 64
ctctgtgagt cggctaga                                                    18

<210> SEQ ID NO 65
<211> LENGTH: 19
<212> TYPE: DNA
<213> ORGANISM: Artificial Sequence
<220> FEATURE:
<223> OTHER INFORMATION: Synthetic Construct

<400> SEQUENCE: 65
ggcgtagttg tatctctga                                                   19

<210> SEQ ID NO 66
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (13)..(13)
<223> OTHER INFORMATION: n is a, c, g, or t

<400> SEQUENCE: 66
agycggagat gancgacaac ac                                              22

<210> SEQ ID NO 67
<211> LENGTH: 19
<212> TYPE: DNA
<213> ORGANISM: Artificial Sequence
<220> FEATURE:
<223> OTHER INFORMATION: Synthetic Construct

<400> SEQUENCE: 67
gcatctgwat taacaaatg                                                  19

<210> SEQ ID NO 68
<211> LENGTH: 18
<212> TYPE: DNA
<213> ORGANISM: Artificial Sequence
<220> FEATURE:
<223> OTHER INFORMATION: Synthetic Construct

<400> SEQUENCE: 68
ccactacgtt atctkgag                                                   18

<210> SEQ ID NO 69
<211> LENGTH: 22
<212> TYPE: DNA
<213> ORGANISM: Artificial Sequence
<220> FEATURE:
<223> OTHER INFORMATION: Synthetic Construct

<400> SEQUENCE: 69
tgtggcttga accttaccgt ct                                              22

<210> SEQ ID NO 70
<211> LENGTH: 20
<212> TYPE: DNA
<213> ORGANISM: Artificial Sequence
<220> FEATURE:
<223> OTHER INFORMATION: Synthetic Construct

<400> SEQUENCE: 70
agccaatagc tavctccgct                                                 20

<210> SEQ ID NO 71
<211> LENGTH: 25
<212> TYPE: DNA
<213> ORGANISM: Artificial Sequence
<220> FEATURE:
<223> OTHER INFORMATION: Synthetic Construct

<400> SEQUENCE: 71
ttaactagcc aatarctaac tccgc                                           25

<210> SEQ ID NO 72
<211> LENGTH: 18

```
<212> TYPE: DNA
<213> ORGANISM: Artificial Sequence
<220> FEATURE:
<223> OTHER INFORMATION: Synthetic Construct

<400> SEQUENCE: 72
gcccaatatt atgcaccc                                                 18

<210> SEQ ID NO 73
<211> LENGTH: 18
<212> TYPE: DNA
<213> ORGANISM: Artificial Sequence
<220> FEATURE:
<223> OTHER INFORMATION: Synthetic Construct

<400> SEQUENCE: 73
gtcgccagtt tccatttg                                                 18

<210> SEQ ID NO 74
<211> LENGTH: 20
<212> TYPE: DNA
<213> ORGANISM: Artificial Sequence
<220> FEATURE:
<223> OTHER INFORMATION: Synthetic Construct

<400> SEQUENCE: 74
ctgagcaccg cattagccgc                                               20

<210> SEQ ID NO 75
<211> LENGTH: 19
<212> TYPE: DNA
<213> ORGANISM: Artificial Sequence
<220> FEATURE:
<223> OTHER INFORMATION: Synthetic Construct

<400> SEQUENCE: 75
ggcttagtag ttcttgaca                                                19

<210> SEQ ID NO 76
<211> LENGTH: 20
<212> TYPE: DNA
<213> ORGANISM: Artificial Sequence
<220> FEATURE:
<223> OTHER INFORMATION: Synthetic Construct

<400> SEQUENCE: 76
cttccattga cagtgaaatc                                               20

<210> SEQ ID NO 77
<211> LENGTH: 23
<212> TYPE: DNA
<213> ORGANISM: Artificial Sequence
<220> FEATURE:
<223> OTHER INFORMATION: Synthetic Construct

<400> SEQUENCE: 77
atctcatcga cactccagct tcc                                           23
```

PRIMERS FOR THE DETECTION AND TYPING OF CARBAPENEMASE-PRODUCING BACTERIAL STRAINS, AND DETECTION METHOD AND KIT

CROSS-REFERENCE TO RELATED APPLICATIONS

This application is filed under the provisions of 35 U.S.C. § 371 and claims the priority of International Patent Application No. PCT/IB2014/000230 filed on 28 Feb. 2014 entitled "Primers for the Detection and Typing of Carbapenemase-Producing Bacterial Strains, and Detection Method and Kit" in the name of Gloria ROYO GARCÍA, et al., which claims priority to Spanish Patent Application No. P201232077 filed on 31 Dec. 2012, both of which are hereby incorporated by reference herein in their entirety.

The present invention refers to primers for rapid detection and/or typing of carbapenemase-producing bacterial strains. Starting from said primers, the invention also discloses a kit for the rapid detection of carbapenemases so as to identify multi-resistant organisms producing said enzymes, to be used in clinical practice for prevention and epidemiologic control of infection outbreaks, for example hospital-acquired infection outbreaks, and to be particularly used in Intensive Care Units and in Neonatal Intensive Care Units (NICU). Finally, the invention also refers to a method for the detection and/or typing of carbapenemase-producing bacterial strains using said primers.

STATE OF THE ART

Biomolecular techniques are used in epidemiology to analyse certain bacterial characteristics suitable as epidemiological markers. Techniques derived from biochemistry, immunology and genetics are included.

Genotypic typing methods are based on the study of chromosomal or extra-chromosomal DNA. The main methods include plasmid analysis, restriction endonuclease analysis, DNA-probe fingerprinting and PCR-based fingerprinting. With regards to polymerase chain reaction or PCR techniques, there are several PCR variations that can be used. One of them consists of using primers complementary to repetitive regions found in the bacterial genome, and it features two modalities (REP-PCR and ERIC-PCR). Another variation is the PCR in which arbitrary primers are used (AP-PCR). Of all these techniques, REP-PCR is the one showing more discrimination and reproducibility capacity, and it may also be used both in gram-negative and gram-positive bacteria. PCR may also be combined with restriction endonucleases technique, obtaining fragments which are then electrophoretically analysed (PCR-RFLP).

PCR and other amplification techniques may have a deep effect on reducing time to and increasing certainty of diagnosis for a variety of microorganism infections. The use of this technique is interesting mainly in those infections for which other alternative methods are costly and troublesome or in which a delay in the diagnosis is caused by the slow growth of microorganisms in conventional culture means.

Nowadays, there is intensive work being carried out on the design of reliable methods for detection of these multi-resistant strains. A bibliographic review carried out by the inventors, shows that there are several research groups working on this important clinical problem.

As a consequence of this research, a surveillance method has been developed so as to identify the presence of carbapenem-resistant KPC-producing enterobacteriaceae in the rectum, based on PCR detection of blakPC gene (Schechner V. Evaluation of PCR-based testing for surveillance of KPC-producing carbapenem-resistant members of the Enterobacteriaceae family. J Clin Microbiol. 2009T; 47:3261-5). The research in question develops a rapid identification system, but it exclusively detects the blackPC gene, which represents a limitation for those media in which other carbapenemases prevail. On the other hand, the research lacks for a "gold" standard for comparison of the method, so the actual sensitivity values could be lower than those obtained experimentally.

Likewise, there are homologous systems for detection of the blaNDM-1 gene (Danny C. T. Ong. Rapid detection of the blaNDM-1 gene by real-time PCR. J. Antimicrob. Chemother. (2011) doi: 10.1093/jac/dkr184 y Kruttgen A. et al. Real-time PCR assay and a synthetic positive control for the rapid and sensitive detection of the emerging resistance gene New Delhi metallo-β-lactamase-1 (blaNDM-1). Med Microbiol Immunol 2011; 200:137-41).

Finally, there are screening methodologies which, by using boronic acid derivatives, allow the detection of class A carbapenemase-producing bacteria, including KPC, Sme, IMI, NMC-A and GES. This system that can recognize different types of carbapenemases is based, however, on phenotypic microbiological techniques and not in molecular techniques, which are generally faster than the former ones.

Several patents may be cited which are related to the object of the invention:

RU 2415932-A describes a method for gene identification of broad-spectrum class A β-lactamases. The method is based on PCR technique and uses a DNA microchip labelled with biotin; this molecule is detected by a streptavidin-peroxidase conjugate, subsequently recognized by means of colorimetric detection of peroxidase.

WO2008124670-A refers to a method for identification of all known isoforms of KPC gene, which includes a new pair of primers and a new probe for enzyme detection by means of amplification methods such as PCR technique. This system may be presented in the form of a kit for detection of carbapenemases in samples from patients. The system described herein is the closest to that disclosed in the present invention but it is much more limited, since it only detects KPC carbapenemases.

Therefore, there is a need for developing systems that allow a simple, rapid and reliable detection of carbapenemases-producing bacteria in biological samples, which would be interesting from the point of view of clinical diagnosis. It would be also desirable that this system would allow not only typing of detected carbapenemases, but also detection of the greatest number possible thereof.

DESCRIPTION OF THE INVENTION

The invention refers to primers and probes identified in the appended claims. The primers and probes object of this invention may be used for the preparation of a kit for carbapenemase gene identification and detection, preferably carbapenemase genes contained in and produced by carbapenemase-producing bacterial strains. The invention also provides a diagnosis method using said primers and probes.

Another object described in the present invention refers to a kit for carbapenemase gene identification and detection, preferably carbapenemase genes contained in and produced by carbapenemase-producing bacterial strains, comprising the primers and probes according to this invention.

In a preferred embodiment of the invention, the kit comprises primers and probes specific for recognizing different carbapenemase genes, for example those indicated in Table 1, included below.

The invention also comprises a method for detection and typing of carbapenemase-producing bacterial strains, consisting of binding and hybridising the primers of the invention to a specific DNA sequence of the gene to be tested, performing a selective specific amplification of carbapenemase genes and identifying the amplification product with the specific probe of the genetic sequence or genetic fragment of diagnostic interest.

The identification method of carbapenemase genes disclosed in this invention is characterized in that it preferably uses multiplex reactions where, for example, two or three primers-probe reactions work together to detect different types of carbapenemase genes. The reactions that can work together are shown in Table 1.

In particular, the method for carbapenemase genes identification of this invention is characterized in that each forward and reverse primer from a multiplex reaction binds to specific DNA sequences so that they can be PCR amplified, and, preferably, at the same time each specific probe labelled with a determined fluorophore binds to these amplicons which are formed in the case of carbapenemase genes presence.

Thus, DNA sequences are preferably subjected to PCR (polymerase chain reaction technique) which is, more preferably, Multiplex real-time PCR.

The method allows detection of different targets (carbapenemases) in a single reaction and makes it possible to detect a number greater than 170 carbapenemase enzymes being comprised in, but not limited to, the following types:
  Class A carbapenemase: NMC, IMI, SME, KPC and GES.
  Class B1 carbapenemase: IMP, VIM, GIM, SPM, NDM and SIM.
  Class D carbapenemase: OXA-23-like, 51-like, 58-like, 60a-like, 50a-like, 55-like, 62-like, 54-like, 24-like, 48-like, 133-like, 182-like, 98-like, 60c-like and 60d-like.

The main contribution of the invention lies in the oligonucleotide sequences of the disclosed primers, which may be used together in a single amplification reaction allowing the detection of a great number of carbapenemase genes potentially present in a biological sample.

The method does not share the same technology as other commercially available systems which can detect carbapenemases (for example, the products from check-points line), and is preferably based on taqman technology, that is, it is preferably a detection method of carbapenemases by means of Taqman technology.

Thus, the innovation lies in using a series of oligonucleotides designed by the inventors which, combined among them and preferably together with taqman technology, can detect most of the carbapenemases described in the literature, going beyond any system described so far.

The technique, as well as the benefits already mentioned, has other additional advantages as that of being an essay with capacity to be adapted to any laboratory being provided with a PCR thermal cycler, preferably in real time, without the need of exclusive equipment or software, thus reducing costs and increasing accessibility to the technique by any laboratory.

Oligonucleotides disclosed are specific for each group of carbapenemases and have been designed to hybridise against DNA regions conserved for each group, such that all different variants belonging to the same group can be detected with a probe.

The technique used is, preferably, Multiplex real-time PCR which, as it is well known, is a technique being capable of detecting more than one target at the same time in a DNA amplification reaction (PCR). More preferably, each amplicon formed by the amplification reaction with two specific oligonucleotides is distinguished from each other thanks to a third oligonucleotide labelled with a determined fluorophore in such a way that, depending on which fluorophore detects the real-time PCR apparatus in a sample, there will be present one target or the other.

The number of targets that can be detected at the same time is limited by two factors:
1. By the number of spectrally different fluorophores (dyes) commercially available.
2. By the number of fluorophores ("dyes") which can be excited and detected by the apparatus used.

The advantages associated to the described invention are:
1. Detection of the target: different carbapenemase genes are detected from the DNA of the strain that is thought to be carbapenemase-producing. Both genes found in plasmids and genes found in the bacteria chromosome can be detected.
2. Type of sample: although in a preferred embodiment the technique is intended to carry out real-time PCR with DNA extracted from a previously culture-isolated strain, it can also be performed from DNA extracted from a biological sample of any type, e.g. a hemoculture.
3. Quickness: diagnosis time is reduced to approximately 2 hours once the sample is available to be tested/assayed (for example, 35 min for extraction of the DNA contained in the sample and 1 h 20 minutes for PCR). Furthermore, sensitivity and specificity are considerably increased (coefficients very near 1).
4. The method described herein can be used for the detection of any carbapenemase-producing microorganism (gram-positive or gram-negative) during, for example, an infectious process, allowing the doctor to be able to make a better choice of the antibiotic therapy (reducing the therapeutic failure rate).
5. Regarding the control of hospital-acquired infection outbreaks, it is considered that, in the event a hospital outbreak is suspected to be taking place, applying this system could be fundamental for cost and time saving when detecting where said outbreak comes from. As it is capable of detecting and classifying the carbapenemases by classes, it could be possible to locate where the outbreak comes from and take actions quickly, reducing the potential danger being caused by said outbreak.

Regarding knowledge about the epidemiology of the area where a carbapenemase-producing strain research is done, it should be noted that currently, since there are not quality detection methods, the distribution and the type of carbapenemases in our environment is unknown.

For all that, a first aspect of the invention refers to a pair of primers, hereinafter "pair of primers of the invention", for detection and typing of carbapanemase-producing bacterial strains, selected from the list consisting of: SEQ ID NO: 67-SEQ ID NO: 68, SEQ ID NO: 1-SEQ ID NO: 2, SEQ ID NO: 4-SEQ ID NO: 5, SEQ ID NO: 7-SEQ ID NO: 8, SEQ ID NO: 10-SEQ ID NO: 11, SEQ ID NO: 13-SEQ ID NO: 14, SEQ ID NO: 16-SEQ ID NO: 17, SEQ NO: 19-SEQ ID NO: 20, SEQ ID NO: 22-SEQ ID NO: 23, SEQ ID NO: 25-SEQ ID NO: 26, SEQ ID NO: 28-SEQ ID NO: 29, SEQ ID NO: 31-SEQ ID NO: 32, SEQ ID NO: 34-SEQ ID NO:

35, SEQ ID NO: 37-SEQ ID NO: 38, SEQ ID NO: 40-SEQ ID NO: 41, SEQ ID NO: 43-SEQ ID NO: 44, SEQ ID NO: 46-SEQ ID NO: 47, SEQ ID NO: 49-SEQ ID NO: 50, SEQ ID NO: 52-SEQ ID NO: 53, SEQ ID NO: 55-SEQ ID NO: 56, SEQ ID NO: 58-SEQ ID NO: 59, SEQ ID NO: 61-SEQ ID NO: 62, SEQ ID NO: 64-SEQ ID NO: 65, SEQ ID NO: 72-SEQ ID NO: 73 and SEQ ID NO: 75-SEQ ID NO: 76.

Table 1, shown below, indicates what type of cabapenemase is capable of amplifying each one of these pairs of primers.

Another aspect of the invention refers to a kit, hereinafter "kit of the invention", to be used in the detection of carbapenemase encoding genes, comprising at least a pair of primers of the invention and reagents required to perform an amplification reaction. Preferably, said kit comprises at least a probe capable of hybridization to the amplification product of said pair of primers.

By "reagents required to perform an amplification reaction" is meant, without limitation, the use of buffers, enzymes, polymerase enzymes, cofactors to obtain an optimal activity thereof, agents to prevent contamination, etc. On the other hand, the kit may include all supports and recipients necessary for its operation and optimisation. The kit may also contain other molecules, genes, proteins or probes of interest, which are suitable as negative and positive controls. Preferably, the kit also comprises instructions to perform the method of the invention described above.

The expression "probe", "primer" and "diagnostic genetic fragment" indicate, in the present text, the nucleotide sequence specific to recognize or detect selectively carbapenemase encoding genes, contained and produced by bacterial strains. The primers are used to activate an amplification reaction of a DNA fragment, preferably by polymerase chain reaction or PCR. The probe is used for specific detection of the target of interest formed by said amplification reaction, preferably PCR, and its sequence will be complementary to that of said target of interest or amplification product produced by the pair of primers of the invention.

Primers, according to this invention, are sequences of oligonucleotides used as forward primer or reverse primer to activate the amplification reaction, preferably PCR, with the characteristic of binding specific regions of carbapenemases.

The term "hybridises" or "hybridization" as used herein, refers to a process in which two complementary strands of nucleic acid recognize each other, and bind under appropriate astringency conditions. Hybridizations to which the present invention refer to are carried out typically and preferably with nucleic acid sequences having a length between 10-100 nucleotides, more preferably between 10-50 nucleotides, even more preferably between 10-30 nucleotides. The techniques and conditions of hybridization of nucleic acids are well known in the art. The average expert in the matter is capable of estimating and adjusting the rigor of the hybridization conditions.

In a preferred embodiment, the kit of the invention, the pair of primers of the invention or the probe is labelled with a fluorophore.

"Fluorophore" is understood to be any compound which can emit a light or coloured signal after being excited. Examples of fluorophores include, but are not limited to: fluorescein, rhodamine, coumarin, cyanine, and derivatives thereof, GFP, YFP and RFP, oregon green, eosin, Texas red, naphthalene derivatives, coumarin derivatives, oxadiazol derivatives, pyrene derivatives, oxacin derivatives (as Nile red or Nile blue), acridine derivatives, tetrapyrrole, Alexa Fluor, DyLight Fluor, CY5, TAMRA, JOE or biotin. In a more preferred embodiment, the probe is labelled with CY5, TAMRA or JOE. In another preferred embodiment, at least one of the primers in the pair of primers of the invention is labelled with biotin.

In another preferred embodiment of the kit of the invention, the probe comprises, more preferably consists of, the sequence:
  a. SEQ ID NO: 3, when the pair of primers is SEQ ID NO: 1-SEQ ID NO: 2,
  b. SEQ ID NO: 6, when the pair of primers is SEQ ID NO: 4-SEQ ID NO: 5,
  c. SEQ ID NO: 9, when the pair of primers is SEQ ID NO: 7-SEQ ID NO: 8,
  d. SEQ ID NO: 12, when the pair of primers is SEQ ID NO: 10-SEQ ID NO: 11,
  e. SEQ ID NO: 15, when the pair of primers is SEQ ID NO: 13-SEQ ID NO: 14,
  f. SEQ ID NO: 18, when the pair of primers is SEQ ID NO: 16-SEQ ID NO: 17,
  g. SEQ ID NO: 21, when the pair of primers is SEQ ID NO: 19-SEQ ID NO: 20,
  h. SEQ ID NO: 24, when the pair of primers is SEQ ID NO: 22-SEQ ID NO: 23,
  i. SEQ ID NO: 27, when the pair of primers is SEQ ID NO: 25-SEQ ID NO: 26,
  j. SEQ ID NO: 30, when the pair of primers is SEQ ID NO: 28-SEQ ID NO: 29,
  k. SEQ ID NO: 33, when the pair of primers is SEQ ID NO: 31-SEQ ID NO: NO: 32,
  l. SEQ ID NO: 36, when the pair of primers is SEQ ID NO: 34-SEQ ID NO: 35,
  m. SEQ ID NO: 39, when the pair of primers is SEQ ID NO: 37-SEQ ID NO: 38,
  n. SEQ ID NO: 42, when the pair of primers is SEQ ID NO: 40-SEQ ID NO: 41,
  o. SEQ ID NO: 45, when the pair of primers is SEQ ID NO: 43-SEQ ID NO: 44,
  p. SEQ ID NO: 48, when the pair of primers is SEQ ID NO: 46-SEQ ID NO: 47,
  q. SEQ ID NO: 51, when the pair of primers is SEQ ID NO: 49-SEQ ID NO: 50,
  r. SEQ ID NO: 54, when the pair of primers is SEQ ID NO: 52-SEQ ID NO: 53,
  s. SEQ ID NO: 57, when the pair of primers is SEQ ID NO: 55-SEQ ID NO: 56,
  t. SEQ ID NO: 60, when the pair of primers is SEQ ID NO: 58-SEQ ID NO: 59,
  u. SEQ ID NO: 63, when the pair of primers is SEQ ID NO: 61-SEQ ID NO: 62,
  v. SEQ ID NO: 66, when the pair of primers is SEQ ID NO: 64-SEQ ID NO: 65,
  w. SEQ ID NO: 69, SEQ ID NO: 70 and/or SEQ ID NO: 71, when the pair of primers is SEQ ID NO: 67-SEQ ID NO: 68,
  x. SEQ ID NO: 74, when the pair of primers is SEQ ID NO: 72-SEQ ID NO: 73, or
  y. SEQ ID NO: 77, when the pair of primers is SEQ ID NO: 75-SEQ ID NO: 76.

In another preferred embodiment, the kit of the invention comprises the pairs of primers SEQ ID NO: 28-SEQ ID NO: 29, SEQ ID NO: 46-SEQ ID NO: 47, SEQ ID NO: 55-SEQ ID NO: 56, SEQ ID NO: 67-SEQ ID NO: 68 and SEQ ID NO: 72-SEQ ID NO: 73 and probes capable of hybridising with the amplification products of said pairs of primers, more preferably the probes of SEQ ID NO: 30, SEQ ID NO: 48, SEQ ID NO: 57, SEQ ID NO: 69, SEQ ID NO: 70, SEQ ID NO: 71 and SEQ ID NO: 74. These pairs of primers are capable of amplifying type KPC carbapenemases (class A), OXA-48 (class D) and NDM, IMP and VIM (class B) (see Table 1).

In an even more preferred embodiment, the kit of the invention comprises all the pairs of primers of the invention, that is, the pairs or primers SEQ ID NO: 67-SEQ ID NO: 68, SEQ ID NO: 1-SEQ ID NO: 2, SEQ ID NO: 4-SEQ ID NO: 5, SEQ ID NO: 7-SEQ ID NO: 8, SEQ ID NO: 10-SEQ ID NO: 11, SEQ ID NO: 13-SEQ ID NO: 14, SEQ ID NO: 16-SEQ ID NO: 17, SEQ ID NO: 19-SEQ ID NO: 20, SEQ ID NO: 22-SEQ ID NO: 23, SEQ ID NO: 25-SEQ ID NO: 26, SEQ ID NO: 28-SEQ ID NO: 29, SEQ ID NO: 31-SEQ ID NO: 32, SEQ ID NO: 34-SEQ ID NO: 35, SEQ ID NO: 37-SEQ ID NO: 38, SEQ ID NO: 40-SEQ ID NO: 41, SEQ ID NO: 43-SEQ ID NO: 44, SEQ ID NO: 46-SEQ ID NO: 47, SEQ ID NO: 49-SEQ ID NO: 50, SEQ ID NO: 52-SEQ ID NO: 53, SEQ ID NO: 55-SEQ ID NO: 56, SEQ ID NO: 58-SEQ ID NO: 59, SEQ ID NO: 61-SEQ ID NO: 62, SEQ ID NO: 64-SEQ ID NO: 65, SEQ ID NO: 72-SEQ ID NO: 73 and SEQ ID NO: 75-SEQ ID NO: 76, and probes capable of hybridise to the amplification products of said pairs of primers, preferably the probes described above in sections (a) and (y).

The pairs of primers of the invention and the kit of the invention are useful for detection and/or typing of carbapenemase genes in biological samples, such that they can be used in a diagnostic method in vitro where if presence of said genes is detected, it can be stated that the tested sample is infected with bacteria producing them. Thus, another aspect of the invention refers to the use in vitro of the pair of primers of the invention or the kit of the invention, for the detection and/or typing of carbapenemase-producing bacterial strains. Examples of carbapenemase-producing bacterial strains include, but are not limited to, *Acinetobacter baumanii, Pseduomonas* sp., those bacteria that belong to the Enterobacteriaceae family (hereinafter Carbapenemase-Producing Enterobacteriaceae CPE), among which *Klebsiella pneumoniae, Escherichia coli, Proteus mirabilis, Enterobacter* spp., *Serratia marcescens, Morganella moraganii,* or *Citrobacter* spp can be cited.

Infection caused by carbapenemase-producing bacteria may be treated with specific antimicrobial agents or any combination thereof. The preferred antimicrobial agents for treatment of CPE infections are selected from the list comprising: Carbapenems (preferably meropenem and doripenem), Aztreonam, Colistin, Aminoglycosides (preferably Amikacin), Fosfomycin, Tigecycline, Quinolones (preferably Ciprofloxacin) or Trimethoprim/Sulfamethoxazole.

In order to choose the antimicrobial agents to be used, it is necessary to consider the typing of the bacterium or bacteria causing the infection, and alternatively to determine the microbiological activity thereof to the antimicrobial agent (for example, determining the minimum inhibitory concentration, MIC). The choice of the treatment with the aforementioned antimicrobial agent, or with any combination of the mentioned antimicrobial agents, as well as concentrations thereof, could be determined by the expert in the art once the carbapenemase-producing bacterial species and/or the concrete strain present in the analysed sample are identified, as it is described in the present invention.

In a preferred embodiment, the carbapenemases are selected from the list consisting of:
Class A carbapenemase, preferably NMC, IMI, SME, KPC and/or GES,
Class B1 carbapenemase, preferably IMP, VIM, GIM, SPM, NDM and/or SIM, and/or Class D carbapenemase, preferably OXA-23-like, 51-like, 58-like, 60a-like, 50a-like, 55-like, 62-like, 54-like, 24-like, 48-like, 133-like, 182-like, 98-like, 60c-like and/or 60d-like.

Another aspect of the invention refers to a method in vitro for detection and/or typing of carbapenemase-producing bacterial strains in an isolated biological sample, characterized in that it comprises:
i. contacting an isolated biological sample comprising DNA with at least a pair of primers of the invention,
ii. amplifying the DNA comprised in said isolated biological sample with the pair of primers, and
iii. detecting the presence of the amplification product obtained in step (ii).

Hereinafter, this method will be referred to as "the method of the invention".

In a preferred embodiment of the method of the invention, detection of step (iii) comprises hybridization of the amplification product obtained in step (ii) to at least a probe capable of hybridising to the amplification product of the pair of primers used in step (i).

In another preferred embodiment, the probe used in the method of the invention or present in the kit of the invention may be fixed on a support, in such a way that the product resulting from amplification of step (ii) is subsequently passed over said support on which the probe is fixed for detection thereof. The term "fixed" as it is used in the present description, refers to the fact that the probe can be attached to a support without losing its activity. Preferably, the support may be an array surface (for example a nylon array), of a membrane, a microtiter plate (for example, 96 wells) or a similar plastic support, or beads (spheres, for example, agarose spheres or small superparamagnetic microspheres consisting of biodegradable arrays).

In another preferred embodiment of the method of the invention, the pair of primers used in step (i) or the probe used for detection in step (iii) is labelled with a fluorophore. In an even more preferred embodiment, the fluorophore is selected from the list consisting of: CY5, TAMRA, JOE and biotin. In an even more preferred embodiment, at least one of the primers in the pair of primers of the invention is labelled with biotin.

In another preferred embodiment of the method of the invention, the probe comprises, more preferably consists of, the sequence:
a. SEQ ID NO: 3, when the pair of primers is SEQ ID NO: 1-SEQ ID NO: 2,
b. SEQ ID NO: 6, when the pair of primers is SEQ ID NO: 4-SEQ ID NO: 5,
c. SEQ ID NO: 9, when the pair of primers is SEQ ID NO: 7-SEQ ID NO: 8,
d. SEQ ID NO: 12, when the pair of primers is SEQ ID NO: 10-SEQ ID NO: 11,
e. SEQ ID NO: 15, when the pair of primers is SEQ ID NO: 13-SEQ ID NO: 14,
f. SEQ ID NO: 18, when the pair of primers is SEQ ID NO: 16-SEQ ID NO: 17,
g. SEQ ID NO: 21, when the pair of primers is SEQ ID NO: 19-SEQ ID NO: 20,
h. SEQ ID NO: 24, when the pair of primers is SEQ ID NO: 22-SEQ ID NO: 23,
i. SEQ ID NO: 27, when the pair of primers is SEQ ID NO: 25-SEQ ID NO: 26,
j. SEQ ID NO: 30, when the pair of primers is SEQ ID NO: 28-SEQ ID NO: 29,
k. SEQ ID NO: 33, when the pair of primers is SEQ ID NO: 31-SEQ ID NO: 32, l. SEQ ID NO: 36, when the pair of primers is SEQ ID NO: 34-SEQ ID NO: 35,
m. SEQ ID NO: 39, when the pair of primers is SEQ ID NO: 37-SEQ ID NO: 38,
n. SEQ ID NO: 42, when the pair of primers is SEQ ID NO: 40-SEQ ID NO: 41,
o. SEQ ID NO: 45, when the pair of primers is SEQ ID NO: 43-SEQ ID NO: 44,
p. SEQ ID NO: 48, when the pair of primers is SEQ ID NO: 46-SEQ ID NO: 47,
q. SEQ ID NO: NO: 51, when the pair of primers is SEQ ID NO: 49-SEQ ID NO: 50,
r. SEQ ID NO: 54, when the pair of primers is SEQ ID NO: 52-SEQ ID NO: 53,
s. SEQ ID NO: 57, when the pair of primers is SEQ ID NO: 55-SEQ ID NO: 56,
t. SEQ ID NO: 60, when the pair of primers is SEQ ID NO: 58-SEQ ID NO: 59,
u. SEQ ID NO: 63, when the pair of primers is SEQ ID NO: 61-SEQ ID NO: 62,
v. SEQ ID NO: 66, when the pair of primers is SEQ ID NO: 64-SEQ ID NO: 65,
w. SEQ ID NO: 69, SEQ ID NO: 70 and/or SEQ ID NO: 71, when the pair of primers is SEQ ID NO: 67-SEQ ID NO: 68,
x. SEQ ID NO: 74, when the pair of primers is SEQ ID NO: 72-SEQ ID NO: 73, or
y. SEQ ID NO: 77, when the pair of primers is SEQ ID NO: 75-SEQ ID NO: 76.

In another preferred embodiment of the method of the invention, in step (i) the isolated biological sample is contacted with the pairs of primers SEQ ID NO: 28-SEQ ID NO: 29, SEQ ID NO: 46-SEQ ID NO: 47, SEQ ID NO: 55-SEQ ID NO: 56, SEQ ID NO: 67-SEQ ID NO: 68 and SEQ ID NO: 72-SEQ ID NO: 73. In a more preferred embodiment, in step (i) the isolated biological sample is contacted with all the pairs of primers of the invention.

In another preferred embodiment, the amplification of step (ii) is carried out by PCR, more preferably real-time PCR and even more preferably Multiplex real-time PCR.

According to the present invention, the term "multiplex" indicates a mixture constitution capable of detecting different classes of carbapenemases in a single reaction (for example, "Oxa-like number", "VIM-GIM-SPM, "KPC_S-ME_NMC").

The term "isolated biological sample comprising DNA", as it is used in the description, refers to, but is not limited to, tissues and/or biological fluids from any origin obtained by means of any method known by an expert in the art which is suitable for such a purpose. The biological sample may come from a floor, water, tissue sample (such as for example, but not limited to, skin), for example from, but not limited to, a biopsy or fine needle aspiration, or it may be a biological fluid, for example, but not limited to, blood, sputum, plasma, serum, urine or exudate (for example, rectal, pus). The sample may also come from an in vitro culture, as for example, but not limited to, from a hemoculture previously inoculated with blood from an individual, preferably with bacteraemia. The sample may be taken from a human, but also from non-human mammals, such as for example, but not limited to, rodents, ruminants, felines or canidae. Thus, in another preferred embodiment of this aspect of the invention, the biological sample comes from an individual, more preferably from a human individual. In another preferred embodiment, the biological sample is blood, sputum, exudate, skin or henoculture previously inoculated with blood from an individual preferably having bacteraemia.

In another preferred embodiment, the method of the invention is a diagnosis method in vitro also comprising:
(iv) assigning the individual to the group of patients infected with carbapenemase-producing bacterial strains when in step (iii) the presence of the amplification product is detected.

The steps of the method of the invention may be completely or partially automated, for example, but not limited to, by means of robotic equipment for detection, in step (iii), of the amplification product.

As well as the steps specified above, the method of the invention may comprise other additional steps, for example, but not limited to, related to the pre-treatment of the biological sample isolated prior to the analysis thereof, for example with the purpose of extracting the genetic material from that sample.

Furthermore, the method of the invention, as well as the kit of the invention, may additionally comprise primers and probes capable of hybridising, and amplifying in the case of primers, a DNA sequence present in the sample to be tested acting as control.

Throughout the description and the claims, the term "comprise" and its variants does not exclude other technical characteristics, additives, components or steps. For experts in the field, other purposes, advantages and characteristics of the invention will derive in part from the description and in part from the practice of the invention. The following examples and figures are provided for illustration purposes, and are not intended to be limiting of the present invention.

EXAMPLES

Figure 1B:
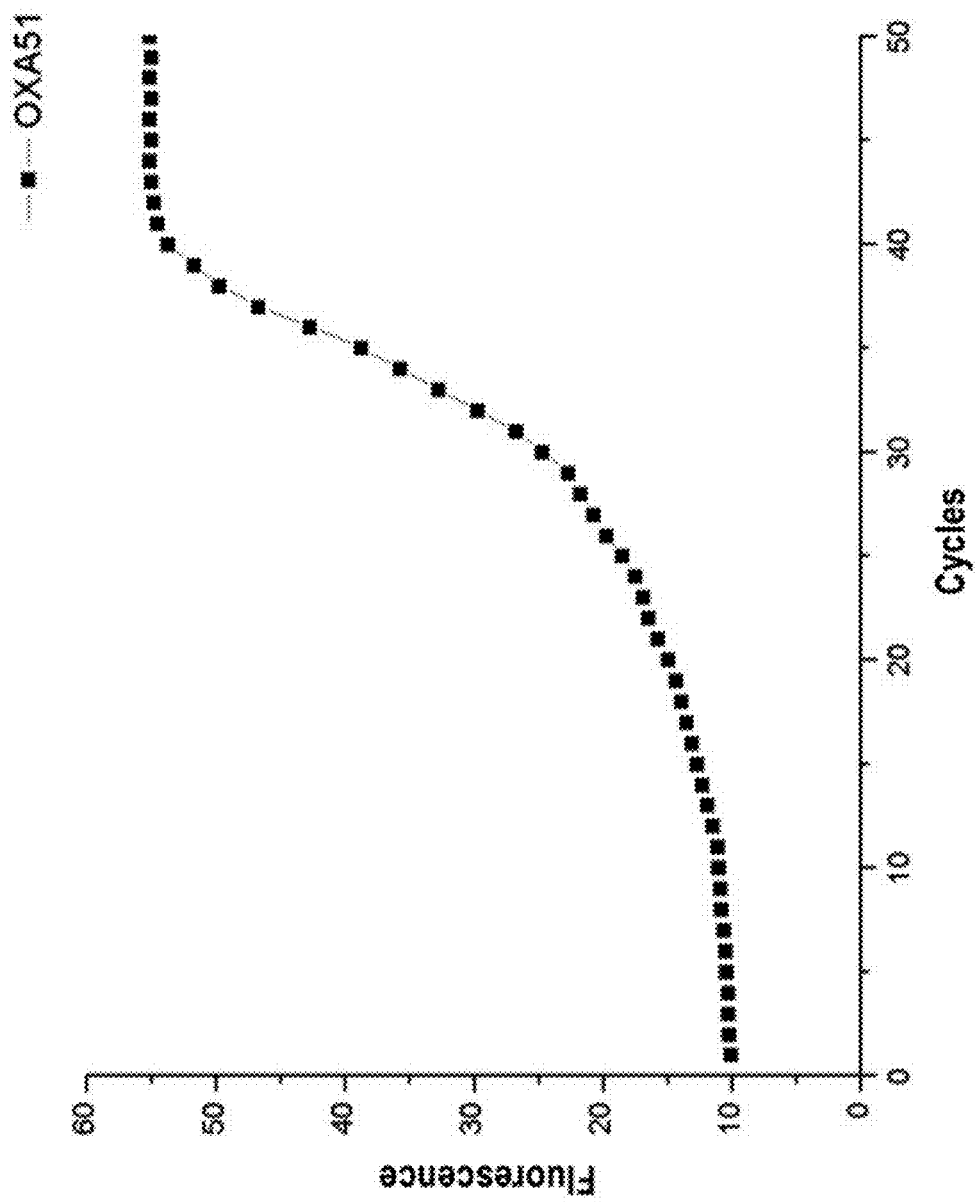
FIG. 1. It shows detection of the carbapenemase groups OXA_23, 51 and 58 in samples containing three different strains of *Acinetobacter baumanii*.

The invention is illustrated below with tests carried out by the inventors demonstrating the effectiveness of the pairs of primers of the invention in detection and/or typing of different groups of carbapenemases.

Example 1

Primers and probes of the present invention have the following sequences selected from the group of: SEQ ID NOs: 1-77 described in Table 1 below. The primers are indicated in the two first columns and the probe is indicated in the third column. In each case, a triplet of two primers and a probe was used for detection.

TABLE 1

| Multiplex_1 | Forward Sequence (F) | Reverse Sequence (R) | Taqman Sequence |
|---|---|---|---|
| Oxa_23_like | TCGGTAATGCTGAAATTG (SEQ ID NO: 1) | CTGTGTATGTGCTAATTGG (SEQ ID NO: 2) | AACTCTACCTCTTGAATAGGCGTAACC (SEQ ID NO: 3) |
| Oxa_51_like | CCTTCAAAATGCTTAATGC (SEQ ID NO: 4) | TAGGGTCATGTCCTTTTC (SEQ ID NO: 5) | CACCATAAGGCAACCACCACAG (SEQ ID NO: 6) |
| Oxa_58_like | TGAGCATAGTATGAGTCG (SEQ ID NO: 7) | TGACCATCATATGTGACA (SEQ ID NO: 8) | TTCCACAAGTGAATAACTCAATCATCG (SEQ ID NO: 9) |
| Multiplex_2 | F Sequence | R Sequence | Taqman Sequence |
| Oxa_60a_like | TGCAGGCTTATGTCGATG (SEQ ID NO: 10) | CTTCGAAAGCGGAAATCTC (SEQ ID NO: 11) | CGCAGCCAGAACTGGTCGATC (SEQ ID NO: 12) |
| Oxa_50a_like | CCTGATCGGCTTATCCAC (SEQ ID NO: 13) | GTACGTTCGATGCCTTGA (SEQ ID NO: 14) | TAGATCCGCCGACGAGGTTCT (SEQ ID NO: 15) |
| Oxa_55_like | AAGCGAGTACTGACTATATYATTC (SEQ ID NO: 16) | CAGGTTAACGGCGAAATAG (SEQ ID NO: 17) | CGTCCAACTCCAACCAACCGA (SEQ ID NO: 18) |
| Multiplex_3 | F Sequence | R Sequence | Taqman Sequence |
| Oxa_62_like | CGATCATTCCCTGGGATG (SEQ ID NO: 19) | GAGACGACCTGATAGCAG (SEQ ID NO: 20) | CCGCGACGCATCAAGAACTG (SEQ ID NO: 21) |
| Oxa_54_like | GCTGTATCATAACAAGTTGC (SEQ ID NO: 22) | CGATCTGAGGCTCAATTC (SEQ ID NO: 23) | CAGTCAGCGTATCGTCAAGCAAG (SEQ ID NO: 24) |
| Oxa_24_like | GTGGGAGAAAGATATGACTTTA (SEQ ID NO: 25) | TCGACCTGTGTTCCAATA (SEQ ID NO: 26) | TGTCAGCAGTTCCAGTATATCAAGAGC (SEQ ID NO: 27) |
| Multiplex_4 | F Sequence | R Sequence | Taqman Sequence |
| Oxa_48_like | GTTGGAATGCTCACTTTAC (SEQ ID NO: 28) | TTCGCCCGTTTAAGATTA (SEQ ID NO: 29) | AATCCTTGCTGCTTATTCTCATTCCA (SEQ ID NO: 30) |
| Oxa_133_like | GAACGTATTGATTTCGGTAA (SEQ ID NO: 31) | CTGTGTATGTGCCAATTG (SEQ ID NO: 32) | AACTCTACCTCTTGAATAGGCGTGA (SEQ ID NO: 33) |
| Oxa_182_like | CCACAAGTAGGTTGGTTAA (SEQ ID NO: 34) | CCCTAAATTTTCTAACGACTTA (SEQ ID NO: 35) | AGAACCAGACATTCCTTGCTTCATT (SEQ ID NO: 36) |
| Multiplex_5 | F Sequence | R Sequence | Taqman Sequence |
| Oxa_98_like | TAGGCGAYGCTATGAAAG (SEQ ID NO: 37) | CTTGGGTACCGATATCTG (SEQ ID NO: 38) | AACCAACACGCTTCACTTCATTAGAC (SEQ ID NO: 39) |
| Oxa_60c_like | CATCGACGTTCAAGATTCC (SEQ ID NO: 40) | CTCCCACTGCTTGTAAGG (SEQ ID NO: 41) | AACAGCCTGATCGCCTTCGA (SEQ ID NO: 42) |
| Oxa_60d_like | GTGCCGATATACCAGGAG (SEQ ID NO: 43) | CTTCGAATGCGGAAATCTC (SEQ ID NO: 44) | CCACGCAGCCAGAATTGATCG (SEQ ID NO: 45) |
| Multiplex_6 | F Sequence | R Sequence | Taqman Sequence |
| VIM | TCCGRCTTTACCAGATTG (SEQ ID NO: 46) | CACGCTGTATCAATCAAA (SEQ ID NO: 47) | CAACTCATCACCATCACGGACAA (SEQ ID NO: 48) |
| GIM | TGGAGTATATCTTCATACCTC (SEQ ID NO: 49) | CTTCGTGTCTTCTTCAGA (SEQ ID NO: 50) | AGGCTTGATTATTATCCAGAACTACCA (SEQ ID NO: 51) |

TABLE 1 -continued

| | | | |
|---|---|---|---|
| SPM | CTTCGAATGTCTTAGT AGC (SEQ ID NO: 52) | TCGGCTTCATAGTCT TAG (SEQ ID NO: 53) | ACCGTTGTCATTGTC TCTTCGC (SEQ ID NO: 54) |
| Multiplex_7 | F Sequence | R Sequence | Taqman Sequence |
| KPC | TTGGCTAAAGGGAAAC AC (SEQ ID NO: 55) | CGACGGCATAGTCAT TTG (SEQ ID NO: 56) | CATACVCTCCGCAGG TTCCG (SEQ ID NO: 57) |
| SME | GGGAATGTTCTCAATG CTA (SEQ ID NO: 58) | CACCTACAACCCAAT CAG (SEQ ID NO: 59) | CGAGCATCACCAGTT GTATTACCTT (SEQ ID NO: 60) |
| NMC | ACCCATCACAACTAAA TATAAAG (SEQ ID NO: 61) | CGTTCAAGRATAATA TTAGTAGCA (SEQ ID NO: 62) | AGCDGCAGCAGCCA TATCAC (SEQ ID NO: 63) |
| Multiplex_8 | F Sequence | R Sequence | Taqman Sequence |
| GES_CARB | CTCTGTGAGTCGGCTA GA (SEQ ID NO: 64) | GGCGTAGTTGTATCT CTGA (SEQ ID NO: 65) | AGYCGGAGATGAICG ACAACAC (SEQ ID NO: 66) |
| Multiplex_9 | F Sequence | R Sequence | Taqman Sequence |
| IMP_3_like | GCATCTGWATTAA CAAATG (SEQ ID NO: 67) | CCACTACGTTATCTKG AG (SEQ ID NO: 68) | TGTGGCTTGAACCT TACCGTCT (SEQ ID NO: 69) |
| IMP_15_like | | | AGCCAATAGCTAVC TCCGCT (SEQ ID NO: 70) |
| IMP_19_like | | | TTAACTAGCCAATAR CTAACTCCGC (SEQ ID NO: 71) |
| Multiplex_10 | F Sequence | R Sequence | Taqman Sequence |
| NDM | GCCCAATATTATG CACCC (SEQ ID NO: 72) | GTCGCCAGTTTCCATT TG (SEQ ID NO: 73) | CTGAGCACCGCATT AGCCGC (SEQ ID NO: 74) |
| SIM | GGCTTAGTAGTTC TTGACA (SEQ ID NO: 75) | CTTCCATTGACAGTGA AATC (SEQ ID NO: 76) | ATCTCATCGACACTC CAGCTTCC (SEQ ID NO: 77) |

Specific oligonucleotides were used for carbapenemases encoding genes. Two oligonucleotides act as forward primer and reverse primer, and a third one was used being labelled with a "dye" or fluorophore and located in the middle of the amplicon which is being synthesized by PCR, and when the taq polymerase passes over it, it cleaves the "dye" which is thus released into the medium emitting its typical fluorescence.

The PCR amplification profile was: pre PCR: 2 min at 50° C., 2 min at 94° C. PCR: (15 seconds at 94° C., 50 seconds at 60° C.)×40 reps. The fluorescence reading was performed in the 50 seconds step at 60° C.

In this invention, different targets may be detected in a single reaction. The experiments performed (meaning by experiment each of the 10 different reactions of target detection realized in several multiplex, in reactions using 2 or 3 different probes in each well of the plate in real-time PCR), have been designed using the programme Beacon Designer v8 under the Taqman experimental profile, having the capacity of generating multiplex reactions upon introducing the different sequences of the desired genes to be amplified at the same time.

In this invention, in order to increase the number of targets which can be detected with the least number of probes possible, the DNA regions conserved among carbapenemases of the same group (ej. KPC, Oxa_23 etc.) were studied, so taking a representative one from each group and focusing on said highly conserved genomic regions, probes capable of detecting most of the variants inside the same group with a single PCR were designed.

A second table (Table 2) is shown below with all the carbapenemases detected by the method disclosed. It should be noted that these are the carbapenemases which the system detects as a minimum, since, considering that the experiment is designed towards conserved DNA regions, it is likely that as new carbapenemases are found which have not been described in the literature yet, as long as they belong to any of the groups detected by the system, they can probably also be detected.

TABLE 2

List of detected carbapenemases and fluorophores thereof

| Class | Type | Sub-type | Labelling |
|---|---|---|---|
| A | GES | 2, 4, 5, 13, 16, 14, 18, 15, 20 | CY5 |
| A | SME | 1, 2, 3 | TAMARA |
| A | KPC | 1, 2, 3, 4, 5, 6, 7, 8, 9, 10, 11 | CY5 |

TABLE 2-continued

List of detected carbapenemases and fluorophores thereof

| Class | Type | Sub-type | Labelling |
|---|---|---|---|
| A | NMC/IMI | 1, 2, 3 | JOE |
| B | IMP | 1, 2, 3, 5, 6, 8, 9, 10, 11, 15, 19, 20, 21, 24, 25, 28, 29, 30 | CY5 TAMARA JOE |
| B | SIM | 1 | TAMARA |
| B | NDM | 1, 2, 5 | CY5 |
| B | VIM | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 | CY5 |
| B | GIM | 1 | TAMARA |
| B | SPM | 1 | JOE |
| D | OXA_23_like | 23, 27, 49, 146, 73, 133, 168, 167, 166, 165, 170, 169, 171, 225 | CY5 |
| D | OXA_51_like | 77, 112, 110, 107, 51, 94, 92, 95, 88, 69, 65, 60, 70, 78, 66, 76, 68, 75, 67, 82, 90, 89, 91, 93, 84, 98, 108, 110, 99, 107, 106, 109, 80, 79, 83, 113, 111, 115, 116, 117, 128, 132, 130, 131, 138, 150, 149, 148, 144, 180, 179, 177, 178, 176, 175, 174, 173, 172, 208, 223, 203, 195, 200, 206, 202, 196, 201, 197, 194 | TAMARA |
| D | OXA_58_like | 58, 97, 96, 164 | JOE |
| D | OXA_48 | 48 | CY5 |
| D | OXA_133 | 133 | TAMARA |
| D | OXA_182 | 182 | JOE |

Example 2. Carbapanemases Detection and Typing System Using Real-Time PCR Combined with Taqman Technology The system designed consists of 25 Taqman probes which, grouped in multiplex reactions of 2 or 3 targets, formed 8 multiplex reactions. In each multiplex reaction each probe was labelled with a different fluorophore, such that the 3 targets could be detected at the same time if they were present in the sample. All the multiplex reactions included in this assay worked under the same temperature conditions and had a minimum score of 8 out of 10, according to the software used for its design, so all combinations worked equally well.

Each probe was designed to hybridise in the PCR reaction against regions highly conserved within a class of carbapenemases. So the system has the capacity to detect all variants within the same group of carbapenemases. In principle, the system is capable of detecting more than 200 known variants.

Obtained results:

As it is shown by the results, the system has the capacity of detecting more than one carbapenemase per reaction. FIG. 3 shows the results obtained from 3 different strains of *Acinetobacter baumanii* from a strain collection, previously well-characterized.

Figure 1C:
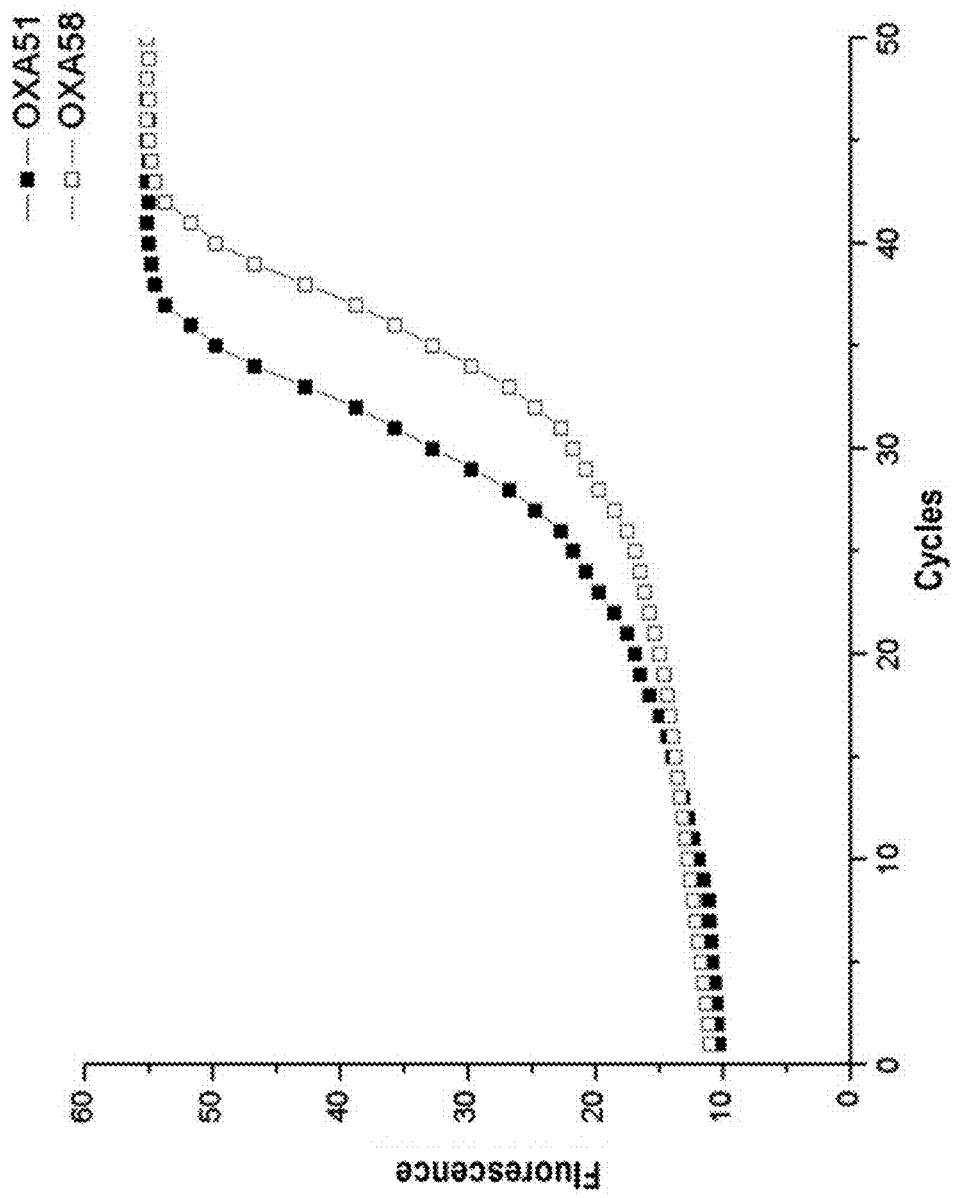

In the first strain 2 types of carbapenemases are found; oxa-23 and oxa-51. In the second strain only carbapenemase oxa-51 is found. In the third strain oxa-58 and oxa-51 are found (FIG. 1).

Apart from setting up the system using commercial strains, the resistance mechanisms of which were already known, additional experiments were also carried out to evaluate the system by means of 2 blind assays. Each assay had a size of 65 and 53 clinical isolates respectively (comprising Enterobacteriaceae, *Pseudomonas* sp. and *Acinetobacter* sp.), previously characterized in different origin hospitals and totally unknown for us. The results obtained by our system showed 100% coincidence with those previously obtained by those institutions.

Additionally, the system was applied to a collection of 600 bacterial strains consecutively isolated, wherein a screening for reduced sensitivity to carbapenems had been previously carried out, with the purpose of getting to know the carbapenemases most frequently found in our environment.

Example 3. Carbapanemases Detection and Typing System Using PCR Technique without Taqman Probes The primers described herein can also be used in a PCR amplification technology, where said primers are labelled with biotin, and a subsequent hybridization against a membrane carrying a DNA fragment complementary to the amplicon of interest. After hybridization, by means of a chemical reaction, the biotin darkens the membrane in the hybridization site, and depending on the darkening extent of the site, a software considers the reaction positive or negative.

Thus, all the primers described herein would get together (without probes in the reaction, only with the biotin labelling of said primers), in a PCR reaction to amplify the targets of interest. That is, instead of performing 8 different reactions of 3 or 2 multiplex each, a single multiplex reaction would be done with all the primers, as described below.

3.1. Adapting Real-Time Amplification to Conventional PCR Amplification and Subsequent Detection of the Product by Hybridization in Biotin-Labelled Amplicon.

A Real-time PCR system to genetically detect carbapenemase-producing strains was designed. The real-time multiplex reactions (grouped in threes), were adapted in a single conventional PCR reaction, wherein instead of carrying out multiplex reactions in groups of three targets, all those reactions were put together in a single reaction, wherein all the primers designed for the real-time PCR system were present. So when a strain is subjected to an assay and is carrying a gene which the system can detect, this is amplified and by means of an analysis in agarose gel it can be determined if it carries or not the carbapenemases, and it is subsequently hybridized in a membrane (with the amplicons being labelled with biotin) to identify what type of carbapenemase it is carrying.

The conventional PCR programme used for amplification was as follows:

1 cycle of 4 min at 94° C., followed by 40 cycles of 30 seconds at 94° C., 45 seconds at 50° C. and 45 seconds at 68° C., and 1 additional cycle of 7 min at 68° C.

Figure 2:
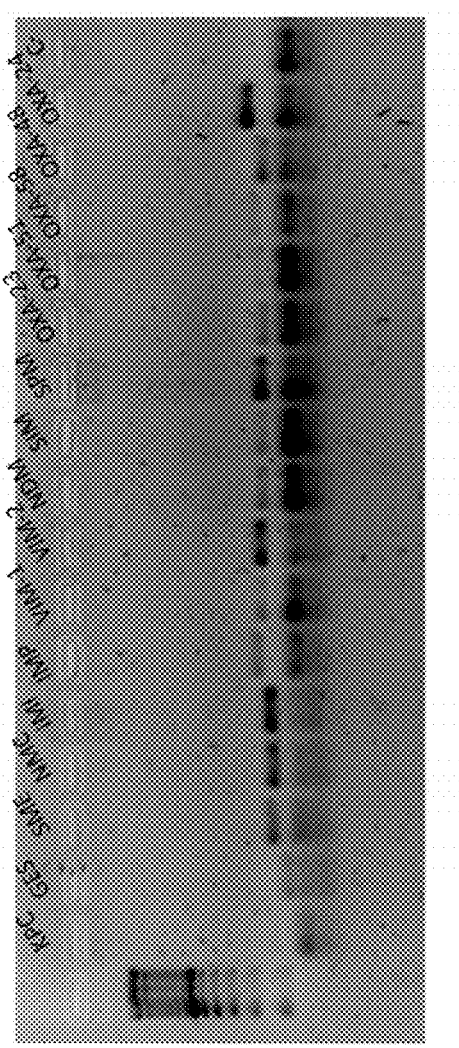
FIG. 2. It represents visualization in agarose gel of the results of the amplification of different carbapenemase genes after amplification reactions with the pairs of primers of the invention.

The most important stage of the programme is that of 45 seconds at 50° C. The primers were designed to work at a range from 50 to 52 grades (theoretical data obtained from simulation programmes). However, said primers could unexpectedly work optimally in assays in temperature ranges from 57° C. to 60° C. Simulation programmes did not predict the primers could work at temperatures higher than 52° C. On the other hand, according to these programmes, it was not expected that in a multiplex reaction with all the primers of the invention together reliable amplification results could be obtained, since unspecific amplifications results were expected because of incompatibility among primers; however, according to the experimental data shown, the combination of all the primers in a multiplex reaction works quite well, not providing unspecific results (FIG. 2).

Primers concentrations used were as follows:

For amplification and detection of carbapenemase genes KPC, GES, IMP, OXA-51 and SME a concentration of at least 0.5 pmol/μl was used for both primers (forward and reverse), and for the rest of the genes (SPM, SIM, OXA-48, OXA-24, NDM, NMC, VIM, OXA-23, OXA-58) a concentration of at least 0.25 pmol/μl, was used for both primers (forward and reverse).

The invention claimed is:

1. A pair of primers consisting of SEQ ID NO: 67-SEQ ID NO: 68.

2. A kit comprising the pair of primers according to claim 1, and reagents required to perform an amplification reaction.

3. The kit according to claim 2, further comprising at least another pair of primers selected from the group consisting of SEQ ID NO: 1-SEQ ID NO: 2, SEQ ID NO: 4-SEQ ID NO: 5, SEQ ID NO: 7-SEQ ID NO: 8, SEQ ID NO: 10-SEQ ID NO: 11, SEQ ID NO: 13-SEQ ID NO: 14, SEQ ID NO: 16-SEQ ID NO: 17, SEQ ID NO: 19-SEQ ID NO: 20, SEQ ID NO: 22-SEQ ID NO: 23, SEQ ID NO: 25-SEQ ID NO: 26, SEQ ID NO: 28-SEQ ID NO: 29, SEQ ID NO: 31-SEQ ID NO: 32, SEQ ID NO: 34-SEQ ID NO: 35, SEQ ID NO: 37-SEQ ID NO: 38, SEQ ID NO: 40-SEQ ID NO: 41, SEQ ID NO: 43-SEQ ID NO: 44, SEQ ID NO: 46-SEQ ID NO: 47, SEQ ID NO: 49-SEQ ID NO: 50, SEQ ID NO: 52-SEQ ID NO: 53, SEQ ID NO: 55-SEQ ID NO: 56, SEQ ID NO: 58-SEQ ID NO: 59, SEQ ID NO: 61-SEQ ID NO: 62, SEQ ID NO: 64-SEQ ID NO: 65, SEQ ID NO: 72-SEQ ID NO: 73, and SEQ ID NO: 75-SEQ ID NO: 76.

4. The kit according to claim 3, further comprising at least a probe capable of hybridizing the amplification product of any of said pair of primers.

5. The kit according to claim 4, wherein the pair of primers or the probe is labelled with a fluorophore.

6. The kit according to claim 5, wherein the fluorophore is selected from the group consisting of cyanine 5 dye, tetramethylrhodamine, 4,5-dichloro-dimethoxy-fluorescein, and biotin.

7. The kit according to claim 4, wherein the probe comprises the sequence SEQ ID NO: 69, SEQ ID NO: 70, and/or SEQ ID NO: 71.

8. The kit according to claim 4, wherein the probe comprises the sequence:
 a. SEQ ID NO: 3, when the pair of primers is SEQ ID NO: 1-SEQ ID NO: 2,
 b. SEQ ID NO: 6, when the pair of primers is SEQ ID NO: 4-SEQ ID NO: 5,
 c. SEQ ID NO: 9, when the pair of primers is SEQ ID NO: 7-SEQ ID NO: 8,
 d. SEQ ID NO: 12, when the pair of primers is SEQ ID NO: 10-SEQ ID NO: 11,
 e. SEQ ID NO: 15, when the pair of primers is SEQ ID NO: 13-SEQ ID NO: 14,
 f. SEQ ID NO: 18, when the pair of primers is SEQ ID NO: 16-SEQ ID NO: 17,
 g. SEQ ID NO: 21, when the pair of primers is SEQ ID NO: 19-SEQ ID NO: 20,
 h. SEQ ID NO: 24, when the pair of primers is SEQ ID NO: 22-SEQ ID NO: 23,
 i. SEQ ID NO: 27, when the pair of primers is SEQ ID NO: 25-SEQ ID NO: 26,
 j. SEQ ID NO: 30, when the pair of primers is SEQ ID NO: 28-SEQ ID NO: 29,
 k. SEQ ID NO: 33, when the pair of primers is SEQ ID NO: 31-SEQ ID NO: 32,
 l. SEQ ID NO: 36, when the pair of primers is SEQ ID NO: 34-SEQ ID NO: 35,
 m. SEQ ID NO: 39, when the pair of primers is SEQ ID NO: 37-SEQ ID NO: 38,
 n. SEQ ID NO: 42, when the pair of primers is SEQ ID NO: 40-SEQ ID NO: 41,
 o. SEQ ID NO: 45, when the pair of primers is SEQ ID NO: 43-SEQ ID NO: 44,
 p. SEQ ID NO: 48, when the pair of primers is SEQ ID NO: 46-SEQ ID NO: 47,
 q. SEQ ID NO: 51, when the pair of primers is SEQ ID NO: 49-SEQ ID NO: 50,
 r. SEQ ID NO: 54, when the pair of primers is SEQ ID NO: 52-SEQ ID NO: 53,
 s. SEQ ID NO: 57, when the pair of primers is SEQ ID NO: 55-SEQ ID NO: 56,
 t. SEQ ID NO: 60, when the pair of primers is SEQ ID NO: 58-SEQ ID NO: 59,
 u. SEQ ID NO: 63, when the pair of primers is SEQ ID NO: 61-SEQ ID NO: 62,
 v. SEQ ID NO: 66, when the pair of primers is SEQ ID NO: 64-SEQ ID NO: 65,
 w. SEQ ID NO: 74, when the pair of primers is SEQ ID NO: 72-SEQ ID NO: 73, or
 x. SEQ ID NO: 77, when the pair of primers is SEQ ID NO: 75-SEQ ID NO: 76.

9. The kit according to claim 3, comprising the pairs of primers SEQ ID NO: 28-SEQ ID NO: 29, SEQ ID NO: 46-SEQ ID NO: 47, SEQ ID NO: 55-SEQ ID NO: 56, SEQ ID NO: 67-SEQ ID NO: 68 and SEQ ID NO: 72-SEQ ID NO: 73.

10. The kit according to claim 3, comprising all the pairs of primers SEQ ID NO:67-SEQ ID NO:68, SEQ ID NO: 1-SEQ ID NO: 2, SEQ ID NO: 4-SEQ ID NO: 5, SEQ ID NO: 7-SEQ ID NO: 8, SEQ ID NO: 10-SEQ ID NO: 11, SEQ ID NO: 13-SEQ ID NO: 14, SEQ ID NO: 16-SEQ ID NO: 17, SEQ ID NO: 19-SEQ ID NO: 20, SEQ ID NO: 22-SEQ ID NO: 23, SEQ ID NO: 25-SEQ ID NO: 26, SEQ ID NO: 28-SEQ ID NO: 29, SEQ ID NO: 31-SEQ ID NO: 32, SEQ ID NO: 34-SEQ ID NO: 35, SEQ ID NO: 37-SEQ ID NO: 38, SEQ ID NO: 40-SEQ ID NO: 41, SEQ ID NO: 43-SEQ ID NO: 44, SEQ ID NO: 46-SEQ ID NO: 47, SEQ ID NO: 49-SEQ ID NO: 50, SEQ ID NO: 52-SEQ ID NO: 53, SEQ ID NO: 55-SEQ ID NO: 56, SEQ ID NO: 58-SEQ ID NO: 59, SEQ ID NO: 61-SEQ ID NO: 62, SEQ ID NO: 64-SEQ ID NO: 65, SEQ ID NO: 72-SEQ ID NO: 73 and SEQ ID NO: 75-SEQ ID NO: 76.

11. An in vitro method for detection and/or typing of IMP_3_like, IMP_15_like and/or IMP_19_like carbapenemase-producing bacterial strains in an isolated biological sample, said method comprising:
 i. contacting an isolated biological sample comprising DNA with the pair of primers according to claim 1,
 ii. amplifying the DNA comprised in said isolated biological sample with the pair of primers, and
 iii. detecting the presence of the amplification product obtained in step (ii), wherein the presence of said amplification product is indicative of the presence of the IMP_3_like, IMP_15_like and/or IMP_19_like carbapenemase-producing bacterial strains in the isolated biological sample.

12. The in vitro method according to claim 11, wherein step (i) additionally comprises contacting the isolated biological sample with a further pair of primers selected from the group consisting of SEQ ID NO: 1-SEQ ID NO: 2, SEQ ID NO: 4-SEQ ID NO: 5, SEQ ID NO: 7-SEQ ID NO: 8, SEQ ID NO: 10-SEQ ID NO: 11, SEQ ID NO: 13-SEQ ID NO: 14, SEQ ID NO: 16-SEQ ID NO: 17, SEQ ID NO: 19-SEQ ID NO: 20, SEQ ID NO: 22-SEQ ID NO: 23, SEQ ID NO: 25-SEQ ID NO: 26, SEQ ID NO: 28-SEQ ID NO: 29, SEQ ID NO: 31-SEQ ID NO: 32, SEQ ID NO: 34-SEQ ID NO: 35, SEQ ID NO: 37-SEQ ID NO: 38, SEQ ID NO: 40-SEQ ID NO: 41, SEQ ID NO: 43-SEQ ID NO: 44, SEQ ID NO: 46-SEQ ID NO: 47, SEQ ID NO: 49-SEQ ID NO: 50, SEQ ID NO: 52-SEQ ID NO: 53, SEQ ID NO: 55-SEQ ID NO: 56, SEQ ID NO: 58-SEQ ID NO: 59, SEQ ID NO: 61-SEQ ID NO: 62, SEQ ID NO: 64-SEQ ID NO: 65, SEQ ID NO: 72-SEQ ID NO: 73, and SEQ ID NO: 75-SEQ ID NO: 76.

13. The in vitro method according to claim 11, wherein detection of step (iii) comprises hybridization of the amplification product obtained in step (ii) with at least a probe capable of hybridizing with the amplification product of the pair of primers used in step (i).

14. The in vitro method according to claim 13, wherein the pair of primers or the probe is labelled with a fluorophore.

15. The in vitro method according to claim 14, wherein the fluorophore is selected from the group consisting of cyanine 5 dye, tetramethylrhodamine, 4,5-dichloro-dimethoxy-fluorescein, and biotin.

16. The in vitro method according to claim 13, wherein the probe comprises the sequence SEQ ID NO: 69, SEQ ID NO: 70, and/or SEQ ID NO: 71.

17. The in vitro method according to claim 13, wherein the probe comprises the sequence:
  a. SEQ ID NO: 3, when the pair of primers is SEQ ID NO: 1-SEQ ID NO: 2,
  b. SEQ ID NO: 6, when the pair of primers is SEQ ID NO: 4-SEQ ID NO: 5,
  c. SEQ ID NO: 9, when the pair of primers is SEQ ID NO: 7-SEQ ID NO: 8,
  d. SEQ ID NO: 12, when the pair of primers is SEQ ID NO: 10-SEQ ID NO: 11,
  e. SEQ ID NO: 15, when the pair of primers is SEQ ID NO: 13-SEQ ID NO: 14,
  f. SEQ ID NO: 18, when the pair of primers is SEQ ID NO: 16-SEQ ID NO: 17,
  g. SEQ ID NO: 21, when the pair of primers is SEQ ID NO: 19-SEQ ID NO: 20,
  h. SEQ ID NO: 24, when the pair of primers is SEQ ID NO: 22-SEQ ID NO: 23,
  i. SEQ ID NO: 27, when the pair of primers is SEQ ID NO: 25-SEQ ID NO: 26,
  j. SEQ ID NO: 30, when the pair of primers is SEQ ID NO: 28-SEQ ID NO: 29,
  k. SEQ ID NO: 33, when the pair of primers is SEQ ID NO: 31-SEQ ID NO: 32,
  l. SEQ ID NO: 36, when the pair of primers is SEQ ID NO: 34-SEQ ID NO: 35,
  m. SEQ ID NO: 39, when the pair of primers is SEQ ID NO: 37-SEQ ID NO: 38,
  n. SEQ ID NO: 42, when the pair of primers is SEQ ID NO: 40-SEQ ID NO: 41,
  o. SEQ ID NO: 45, when the pair of primers is SEQ ID NO: 43-SEQ ID NO: 44,
  p. SEQ ID NO: 48, when the pair of primers is SEQ ID NO: 46-SEQ ID NO: 47,
  q. SEQ ID NO: 51, when the pair of primers is SEQ ID NO: 49-SEQ ID NO: 50,
  r. SEQ ID NO: 54, when the pair of primers is SEQ ID NO: 52-SEQ ID NO: 53,
  s. SEQ ID NO: 57, when the pair of primers is SEQ ID NO: 55-SEQ ID NO: 56,
  t. SEQ ID NO: 60, when the pair of primers is SEQ ID NO: 58-SEQ ID NO: 59,
  u. SEQ ID NO: 63, when the pair of primers is SEQ ID NO: 61-SEQ ID NO: 62,
  v. SEQ ID NO: 66, when the pair of primers is SEQ ID NO: 64-SEQ ID NO: 65,
  w. SEQ ID NO: 74, when the pair of primers is SEQ ID NO: 72-SEQ ID NO: 73, or
  x. SEQ ID NO: 77, when the pair of primers is SEQ ID NO: 75-SEQ ID NO: 76.

18. The in vitro method according to claim 12, comprising in step (i) contacting an isolated biological sample with all the pairs of primers: SEQ ID NO: 28-SEQ ID NO: 29, SEQ ID NO: 46-SEQ ID NO: 47, SEQ ID NO: 55-SEQ ID NO: 56, SEQ ID NO: 67-SEQ ID NO: 68 and SEQ ID NO: 72-SEQ ID NO: 73.

19. The in vitro method according to claim 12, comprising in step (i) contacting an isolated biological sample with all the pairs of primers SEQ ID NO:67-SEQ ID NO:68, SEQ ID NO: 1-SEQ ID NO: 2, SEQ ID NO: 4-SEQ ID NO: 5, SEQ ID NO: 7-SEQ ID NO: 8, SEQ ID NO: 10-SEQ ID NO: 11, SEQ ID NO: 13-SEQ ID NO: 14, SEQ ID NO: 16-SEQ ID NO: 17, SEQ ID NO: 19-SEQ ID NO: 20, SEQ ID NO: 22-SEQ ID NO: 23, SEQ ID NO: 25-SEQ ID NO: 26, SEQ ID NO: 28-SEQ ID NO: 29, SEQ ID NO: 31-SEQ ID NO: 32, SEQ ID NO: 34-SEQ ID NO: 35, SEQ ID NO: 37-SEQ ID NO: 38, SEQ ID NO: 40-SEQ ID NO: 41, SEQ ID NO: 43-SEQ ID NO: 44, SEQ ID NO: 46-SEQ ID NO: 47, SEQ ID NO: 49-SEQ ID NO: 50, SEQ ID NO: 52-SEQ ID NO: 53, SEQ ID NO: 55-SEQ ID NO: 56, SEQ ID NO: 58-SEQ ID NO: 59, SEQ ID NO: 61-SEQ ID NO: 62, SEQ ID NO: 64-SEQ ID NO: 65, SEQ ID NO: 72-SEQ ID NO: 73 and SEQ ID NO: 75-SEQ ID NO: 76.

20. The in vitro method according to claim 11, wherein the amplification step (ii) is carried out by means of PCR.

21. The in vitro method according to claim 11, wherein the biological sample comes from an individual.

22. The in vitro method according to claim 21, wherein the individual is a human.

23. The in vitro method according to claim 21, wherein the biological sample is blood, sputum, exudate, skin or hemoculture previously inoculated with blood from an individual preferably having bacteraemia.

24. The method according to claim 11, further comprising:
  (iv) assigning the individual to the group of patients infected with carbapenemase-producing bacterial strains when in step (iii) the presence of the amplification product is detected.

* * * * *